(12) United States Patent
Hezemans et al.

(10) Patent No.: US 8,717,654 B2
(45) Date of Patent: May 6, 2014

(54) OPTICAL PROBE WITH FEEDBACK CORRECTION

(75) Inventors: Cornelius Antonius Hezemans, Nuenen (NL); Bernardus Hendrikus Wilhelmus Hendriks, Eindhoven (NL); Waltherus Cornelis Jozef Bierhoff, Eindhoven (NL); Augustinus Laurentius Braun, Heeze (NL); Nenad Mihajlovic, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 279 days.

(21) Appl. No.: 13/320,601

(22) PCT Filed: May 10, 2010

(86) PCT No.: PCT/IB2010/052044
§ 371 (c)(1),
(2), (4) Date: Jan. 20, 2012

(87) PCT Pub. No.: WO2010/131181
PCT Pub. Date: Nov. 18, 2010

(65) Prior Publication Data
US 2012/0113491 A1 May 10, 2012

(30) Foreign Application Priority Data
May 15, 2009 (EP) .................................. 09160441

(51) Int. Cl.
*G02B 26/08* (2006.01)
*A61B 5/05* (2006.01)

(52) U.S. Cl.
USPC ................. 359/200.7; 359/198.1; 359/199.3; 359/209.1; 359/210.1; 359/900; 600/424

(58) Field of Classification Search
USPC .......... 359/196.1–200.8, 209.1–215.1, 221.2, 359/225.1, 226.2; 385/12–13, 25
See application file for complete search history.

(56) References Cited

U.S. PATENT DOCUMENTS

| 6,845,190 | B1 | 1/2005 | Smithwick et al. |
| 7,098,871 | B1 | 8/2006 | Tegreene et al. |
| 2006/0013528 | A1 | 1/2006 | Rosman et al. |
| 2007/0278311 | A1 | 12/2007 | Partyka |
| 2011/0201922 | A1* | 8/2011 | Hezemans et al. ............. 600/424 |

FOREIGN PATENT DOCUMENTS

| EP | 1705616 A1 | 9/2006 |
| EP | 1901107 A1 | 3/2008 |
| WO | 2005024496 A2 | 3/2005 |
| WO | 2007135999 A1 | 11/2007 |

\* cited by examiner

*Primary Examiner* — James Phan

(57) ABSTRACT

The present invention relates to an optical probe (1) suitable for miniature applications. An example application is a fiber-based confocal miniaturized microscope. The optical probe comprises a coil-based actuation system (9, 10) comprising drive coils (9) capable of displacing the distal end (3) of an optical guide (2) housed (4) by the optical probe. The probe makes use of a feedback loop which alternate between driving the displacement of the optical guide by driving a current through the drive coils and switching off the current through the drive coils, and while the drive current being switched off, measure the speed of the distal end of the optical guide. The measured speed is compared to the set-point speed, and if a difference is detected, the drive current is adjusted to eliminate, or at least bring down, this difference.

11 Claims, 3 Drawing Sheets

OPTICAL PROBE WITH FEEDBACK CORRECTION

FIELD OF THE INVENTION

The present invention relates to an optical probe suitable for miniature applications. The invention further relates to an optical imaging system and a method of operating the probe.

BACKGROUND OF THE INVENTION

In connection with diagnosis of various diseases, such as various cancer diseases, biopsies are taken. When taking a biopsy and no malignant cells are detected, it is important that it can be ruled out that this is not simply due to that the biopsy was sampled from the wrong site. To increase the certainty of the biopsy sampling, guided biopsy may be used. Such guided biopsy sampling can be based on a number of image modalities, examples include X-ray, CT, MRI, ultrasound and optics.

For many purposes optical imaging by use of a miniaturized needle microscope is used. Imaging by use of needle microscopy has the advantage that it does not involve harmful X-rays or the expensive machinery of CT or MRI scanners. Moreover, it supports integration into the biopsy needle itself, thereby allowing direct visual inspection of the biopsy site prior to, during and after the biopsy.

The European patent application no. 1 901 107 A1 discloses an example of a miniaturized confocal needle microscope comprising a vibrating light transmitter, in the form of a fibre, mounted inside a housing, where the vibration of the transmitter executes a scan pattern, the vibration being based on an actuation system comprising electromagnetic coils and permanent magnets.

A problem with a scanning fibre is that if the true position of the fibre end deviates from the set-point position, the image construction introduces artefacts.

SUMMARY OF THE INVENTION

The inventors of the present invention have realized that one way of avoiding artefacts related to position deviations is to improve the movement of the fibre or optical guide to make sure the optical guide follows the desired path. In an optical probe system where the driving of the movement of the optical guide is based on a coil-based actuation system where current is driven through a coil, there always will be deviations from the linearity between the applied current and the actual position of a moving optical guide. Therefore, just knowing the current is not enough to construct an image without deformations and there is a need for providing a feedback signal that measures positional information of the vibrating fibre, or other relevant optical element, in addition to the applied current of the driving coils. To this end, it is an object of the present invention to provide an optical probe which minimizes, is substantially free from or even avoids artefacts in the image construction from the motion of the probe. It is a further object to provide a probe which is suitable for miniaturization.

Preferably, the invention alleviates, mitigates or eliminates one or more of the above or other disadvantages singly or in any combination.

In a first aspect, the present invention addresses the above needs by providing an optical probe, the probe comprising:
an optical guide having a distal end;
a housing, the optical guide being mounted inside the housing so that the distal end is displaceable with respect to the housing; and
a coil-based actuation system comprising drive coils capable of displacing the distal end by a displacement force induced by driving a drive current through the drive coils;
wherein the drive current comprises a set-point current related to a positional set-point and an adjustment term;
wherein the adjustment term is determined by a feedback loop comprising:
applying the drive current to the drive coils;
temporally switching off the drive current and while the drive current is switched off measure a speed of the distal end; and
comparing the positional set-point and the measured speed by either
deriving from the positional set-point a set-point speed and comparing the set-point speed and the measured speed to derive a difference; or
deriving from the measured speed a measured position, and comparing the positional set-point and the measured position to derive a difference,
and adjusting the drive current if the difference is above a preset level.

The probe comprises an optical guide having a distal end being mounted inside a housing, and where the distal end is displaceable with respect to the housing. In embodiments, the probe is in the form of a needle probe, such as a miniaturized confocal microscope. The displacement, typically in the form of a vibration, is done by means of a coil-based actuation system comprising drive coils inducing a displacement force by driving a drive current through the drive coils. In an embodiment, the optical guide is an optical fibre with free distal end. Free in the sense, that it is free to be displaced with respect to the housing. The optical guide may comprise one or more optical elements.

In the invention, the probe makes use of a feedback loop which alternates between driving the displacement of the optical guide by driving a current through the drive coils and switching off the current through the drive coils, and while the drive current being switched off, measures the speed of the distal end of the optical guide. The measured speed is compared to the positional set-point, and if a difference is detected, the drive current is adjusted to eliminate, or at least bring down, this difference.

The comparison of the positional set-point and the measured speed to derive the difference may be implemented by any suitable means for comparing quantities in an electrical circuit. It is within the capabilities of the skilled persons to set an appropriate preset level. In an embodiment this level may be zero, so that any difference is minimized, in another embodiment, it may be set to be about a detected or estimated noise limit.

Embodiments of the present invention are advantageous for a number of reasons. By alternating between driving the coils and switching off the drive coils while measuring the speed of the distal end, it is rendered possible to use both coils in a system (one coil system for each single direction) for driving and for measurement, a separation of the coil pair into a driving coil and a measurement coil may therefore be avoided. This renders the driving and measuring system far more linear than a system based on the separation of the coils. Further it increases the sensitivity of the actuation system with a factor of almost 4. The resulting lower distortion together with the higher sensitivity makes, at the same dissipation per driving coil, more driving force possible. Since there is no need for separate measurement coils, the system is well-suited for miniaturization as the actuation system may take up less space. Moreover, the production cost is lowered.

The difference may be determined either by deriving from the positional set-point a set-point speed and comparing the set-point speed and the measured speed to derive a difference or deriving from the measured speed a measured position, and comparing the positional set-point and the measured position to derive a difference, It may be advantageous to make use of speed comparison for the feedback loop since in this situation there is no need for integration of the measured speed in order to obtain the position. The feedback loop may thus be faster and implemented in a more direct way than a feedback loop based on comparison in the position.

In an advantageous embodiment, the speed of the distal end is measured by measuring the voltage across the drive coils while the drive current is switched off. The voltage is a measure of the electromotive force, emf, of the drive coils. It is known that the electromotive force is a measure of the speed of an object moving in a magnetic field.

The optical guide may be displaced at a number of frequencies, it may however be advantageous to displace the optical guide at, or close to, the resonance frequency of the probe system. Driving the optical guide at or near the resonance frequency of the probe system may only require moderate drive currents which enables the use of miniaturized coils.

Advantageously, the total loop gain of the feedback loop is larger than 1, such as much larger than 1. In embodiments the loop gain may be as large as possible without jeopardizing the functioning of the loop gain, e.g. the loop gain should not be so high that there is a need for coil protection. It is within the capability of the skilled person to set an appropriate limit of the loop gain. By using a high loop gain it is further ensured that the difference in the positional-related parameter is maintained low, so that the position set-point can be used to determine the position of the distal end with a high degree of certainty.

In an advantageous embodiment, the adjustment term may further comprise a feed-forward term being based on one or more mechanical and/or electrical parameters. The use of a feed-forward term in combination with a feedback term may be relevant in a situation of low loop gain, such as in a situation where the probe system is driven at a non-resonant frequency. The mechanical and electrical parameters may be such parameters as spring constant, the weight of the moving mass, the damping factor of the system, etc.

In applications, the optical probe may form part of an endoscope, a catheter, a biopsy needle, or other similar applications, such as in connection with in-vivo medical inspections, e.g. in connection with cancer diagnosis, monitoring wound healing or studying molecular processes in tissue. It is also contemplated that fields of application may include, but is not limited to, fields where miniature imaging devices are useful, such as in connection with inspection of small-scale devices, etc.

In a second aspect, an optical imaging system is provided by in addition to an optical probe according to the first aspect, the optical system comprises;
    a radiation source optically coupled to the optical probe, the probe being arranged for guiding radiation emitted from the radiation source to a region of interest; and
    a radiation detector optically coupled to the optical probe, the detector being arranged for detecting radiation received from the region of interest.

In a third aspect of the present invention, there is provided a method of operating a probe in accordance with the first aspect of the invention;
    the method comprising:
    applying the drive current to the drive coils;
    temporally switching off the drive current and measuring the speed of the distal end; and
    comparing the positional set-point and the measured speed by either
        deriving from the positional set-point a set-point speed and comparing the set-point speed and the measured speed to derive a difference; or
        deriving from the measured speed a measured position, and comparing the positional set-point and the measured position to derive a difference;
    and adjusting the drive current if the difference is above a preset level.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
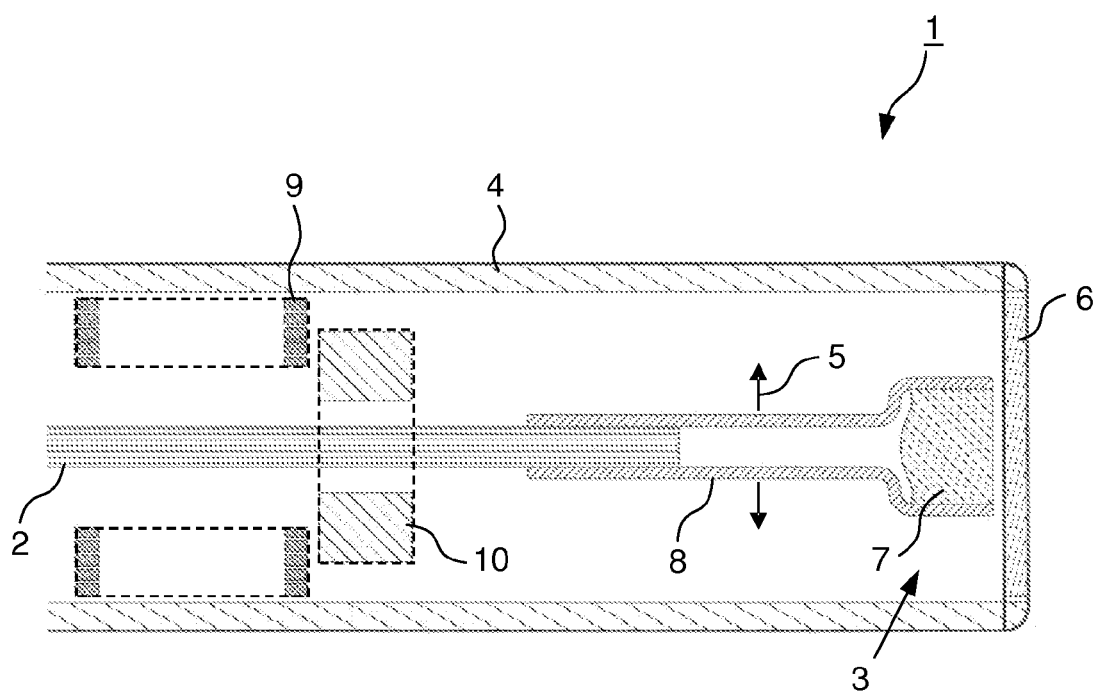
FIG. 1 shows a schematic cross-sectional drawing of a first embodiment of an optical probe.

FIG. 1 is a schematic cross-sectional drawing of an optical probe 1 in accordance with embodiments of the present invention. The optical probe may be in the form of confocal microscope. The optical probe comprises an optical guide 2 having a distal end 3 and a housing 4. The distal end of the optical guide is free to move 5 with respect to the housing in the sense that there is a certain space within the housing in which the end of the optical guide may move. The housing has at its distal end a window 6, such as a glass or polymer window. In the illustrated embodiment, the optical guide comprises a lens system 7 possibly attached to the guide by means of a mount 8. The invention is however not limited by the presence of any specific optical components. The components are merely shown for illustrative purposes. In general any suitable lens system may be used as is known to the skilled person. The optical guide itself is mounted inside the housing by suitable means (not shown) so that the optical guide has a fixed part and a moveable part.

The optical guide may in embodiments be optical fibres (multi-mode and single-mode), thin film optical paths, photonic crystal fibres, photonic band gab fibres (PBG), polarization maintaining fibres, etc. The optical probe may also comprise more than one fibre, i.e. a plurality of fibres or a fibre bundle.

Figure 2:
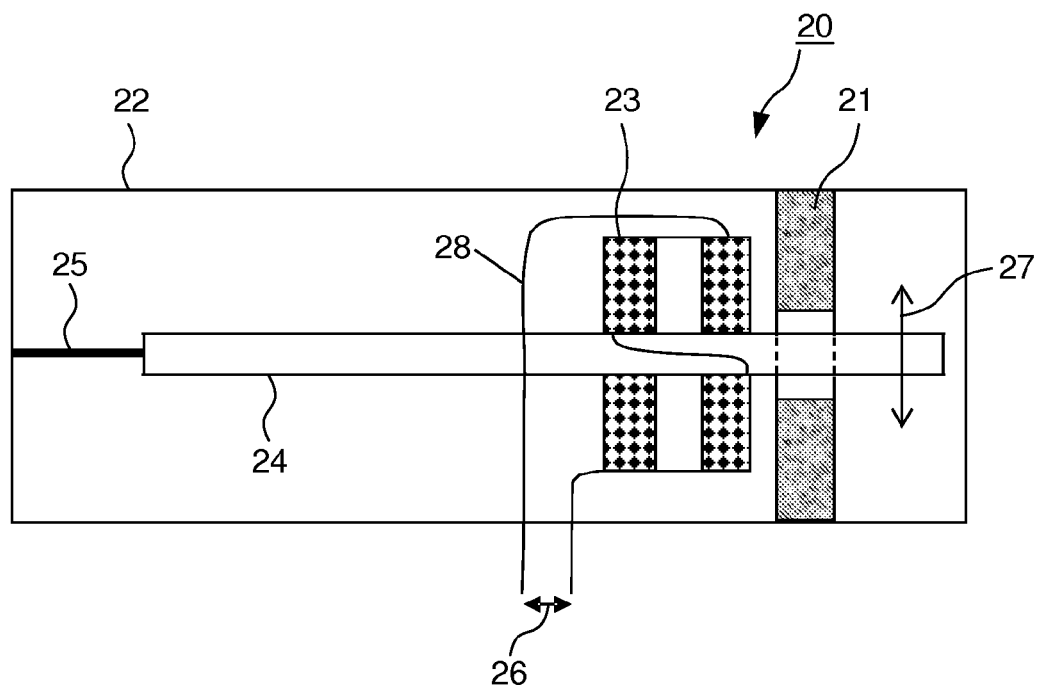
FIG. 2 shows a schematic cross-sectional drawing of a second embodiment of an optical probe.

The optical guide is displaceable by means of a coil-based actuation system 9, 10. The actuation system is capable of displacing the distal end by driving a current through drive coils 9. In the illustrated embodiment, the actuation system comprises a first part comprising an axially polarized magnet 10 and a second part comprising electromagnetic coils 9, where the coils are mounted on the housing and the magnet is mounted on the optical guide. FIG. 2 illustrates the opposite situation where the coils are mounted on the optical guide and the magnet is mounted on the housing. When a current is applied in the coils 9, due to the Lorenz force, the magnet 10 will be pushed away from the centre position depending upon the direction of the current. In this way, the distal end of the optical guide can be placed in any wanted position within the working area of the housing. In embodiments, the magnet 10 is magnetized along the axis of the optical probe. Only a single set of coils are illustrated allowing displacement in a single direction, e.g. along the direction indicated by reference numeral 5. The winding(s) of the coils are in a plane parallel to the axis of the optical guide. A perpendicularly oriented set of coils (not shown) is used for displacement in the direction perpendicular to the illustrated direction 5, moreover a set of coils oriented for displacement along the direction may also be used, such coils are not shown either.

FIG. 2 illustrates a schematic cross-sectional drawing of an optical probe 20. In the Figure the magnet 21 is attached to the housing 22 whereas the coils 23 are attached to an outer par of the optical guide 24. In the illustrated embodiment, the optical guide comprises a core 25 and a flexible support tube 24 for protection of the core. FIG. 2 further illustrates a serial connection 28 of the two coils and the related voltage drop 26 over the two coils. A current through the coils 23 together with the magnetic field from the axially magnetized magnet 21 delivers a force in the direction indicated by reference numeral 27. This force generation system will also generate a back electromotive force, emf, when the coils move in the direction 27 with respect to the magnet. The voltage drop across the wires 26 reflects this emf.

Figure 3:
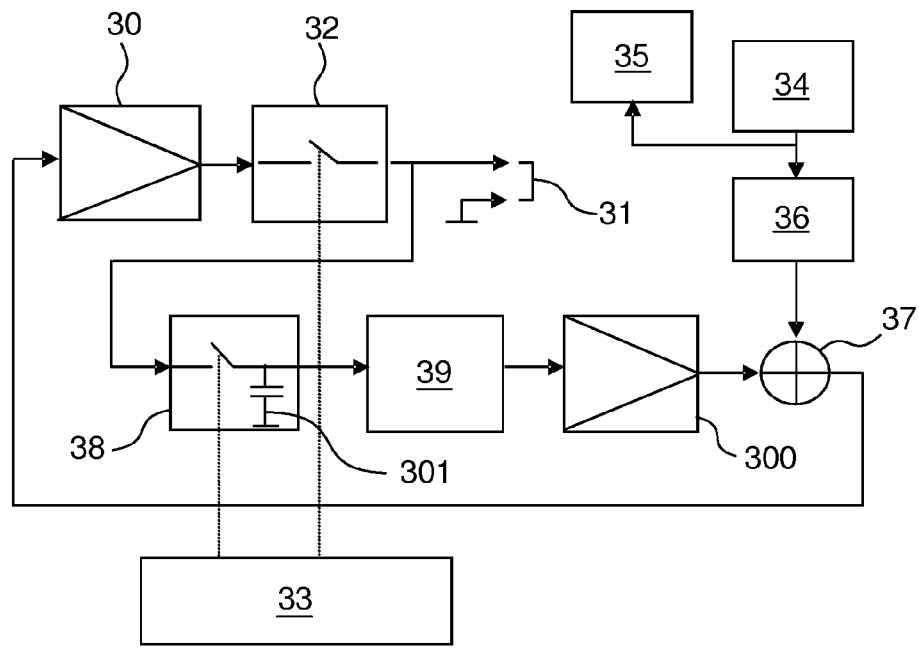
FIG. 3 illustrates a schematic drive circuit with feedback loop.

FIG. 3 illustrates a schematic drive circuit with feedback loop in accordance with embodiments of the present invention. FIG. 3 illustrates the situation where the set-point speed is determined by derivation of the set-point position. A power amplifier 30 delivers the drive current for driving the coils. The coils are electrically connected to the terminals 31. The terminals 31 are separated from the power amplifier 30 by a switch 32 (drive switch) which is controllable by a switch control 33. When switch 32 is closed, the drive current is fed to the coils via the terminals 31. The power amplifier 30 is controlled by a position set-point generator 34. The position set-point generator outputs the desired position of the lens to an image construction unit 35. In an embodiment, the desired drive speed is determined as the derivative of the position. The derivative of the position is determined at a deriver unit 36 and feed into the comparator 37. The output of the comparator 37 is fed into the power amplifier 30 for driving the coils.

If the drive switch 32 is opened, i.e. the drive current is switched off, and the switch 38 is closed, the circuit measures the back emf of the drive coils via the terminals 31. The switch 38 (feedback switch) is controllable by a switch control 33. The measured back emf may be shaped, e.g. by means of a low pass filter 39 and amplified 300 prior to comparison at the comparator 37.

In an embodiment, based on deriving a measured position from the measured speed, and comparing the positional set-point and the measured position, the deriver unit 36 is omitted. Instead an integration unit, or other means for deriving the position from the measured speed is implemented, either as a separate unit inserted between the low pass filter 39 and amplifier 300 or implemented as a part of the low pass filter 39 or amplifier 300.

Figure 4:
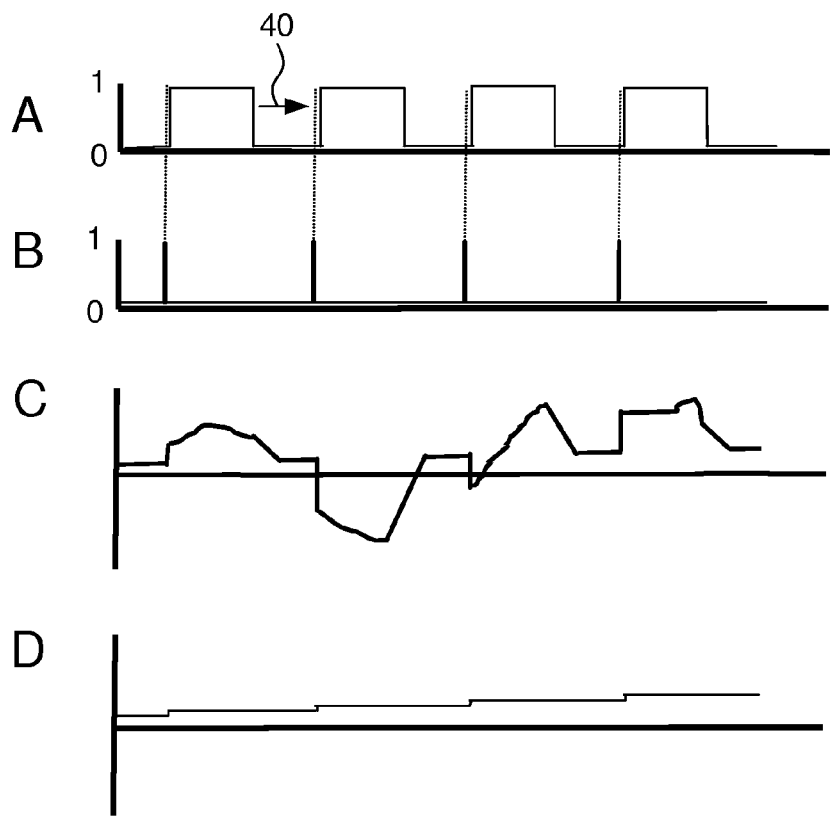
FIGS. 4A and 4B illustrate the operation of the drive switch and feedback switch.
FIGS. 4C and 4D show the voltage across the coils and the output of the zero order sample and hold.

FIGS. 4A and 4B illustrates the operation of the switches 32, 38. A value of one corresponds to closing of the switches, i.e. current can pass the switch, whereas a value of zero corresponds to opening the switches, i.e. no current can pass. The horizontal axis is a time axis. FIG. 4A shows the operation of the drive switch 32, showing that the coils alternatively are provided with drive current and alternatively switched off. FIG. 4B shows the operation of the feedback switch 38, which is briefly closed while the drive current is switched off allowing the feedback circuit to measure the voltage across the terminals 31. The circuit of FIG. 3 ensures that if the speed of the distal end optical guide deviates from the set-point speed, the drive current is adjusted until the measured speed is inline with the set-point speed.

The timing of the opening of the feedback switch 38 after the drive switch 32 has been closed as well as the durations of the open-close states are within the capabilities of the skilled person to set appropriately. In an advantageous embodiment, the feedback switch 38 is however delayed 40 allowing to discharge for the noise of the coils to decrease below an acceptable level. The noise is caused by the energy in the capacities in the switch, wiring, coils and by the self-inductances in coils. The capacitance 301 is a part of the zero order sample and hold circuit. When the feedback switch 38 is switched on, the capacitance is charged with emf, which is proportional to the speed of the optical probe with respect to the housing, and when the feedback switch 38 is switched off, the emf stays at the capacitance so that the voltage can be measured, filtered, amplified and further used for the feedback control. Discharging of the voltage at the coils at the moment when both switches are switched off occurs via the resistance of the switches.

FIGS. 4C and 4D show the voltage across the coils and the output of the zero order sample and hold. FIG. 4C illustrates the voltage of the coils during the course of the switching as illustrated in FIGS. 4A and 4B. In FIG. 4C, firstly the drive switch 38 is open (cf. FIG. 4A) during this period, the measured emf is related only to the movement of the distal end of the optical guide. When the drive switch is closed, the measured emf reflects the driving voltage as feed by the controller, and when the drive switch opens again, the voltage approaches the level where the measured emf again is related only to the speed of the distal end of the optical guide. FIG. 4D shows the output of the zero order sample and hold, each time the feedback switch is opened (cf. FIG. 4B) the voltage jumps due to the charging of the capacitor 301, to the level present at that driving coils at the moment of closing of the feedback switch (cf. FIG. 4C). The speed of the optical probe with respect to the housing is ramp shaped in time as can be seen in FIG. 4D. The horizontal axis is a time axis.

To obtain a small error between the speed-set-point and the actual speed of the distal end, a loop gain much higher than 1 may be needed at the frequencies at which the optical guide is supposed to move. This can be realised by choosing a high overall gain, leading to a high bandwidth or by choosing a relatively low gain and only one frequency to move the optical guide: the resonance frequency. This last choice is particularly advantageous if the damping of the moving mechanics is very low and will lead to a low bandwidth and low dissipation in the coils and yet a low speed error. The speed error can be low enough to reliably use the position-set-point as the position information at resonance frequency. The position of the distal end at non-resonance-frequencies with respect to the not moving part however may be determined by the acceleration forces on the not moving part at these frequencies and the resonance frequency of the distal end.

Figure 5:
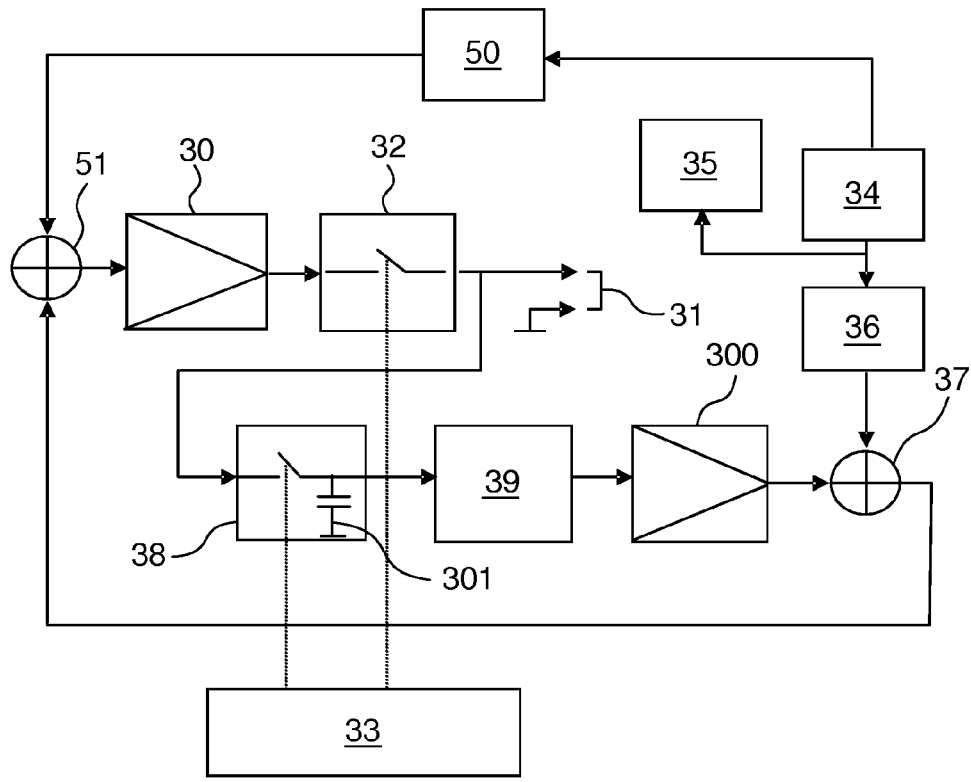
FIG. 5 illustrates a schematic drive circuit with feedback loop in combination with feed-forward loop.

FIG. 5 illustrates a drive circuit with feedback loop in combination with feed-forward loop. The main part of the illustrated circuit is similar as to the one shown in FIG. 3. However, the set-point position 34 is additionally output to a unit 50 for determining a feed-forward term based on one or more mechanical and/or electrical parameters. The feed-forward term is combined with the feedback term at the combiner 51 to input into the power amplifier 30.

The feed-forward term may advantageously by used in connection with driving the system in a non-resonant mode to compensate for the low loop gain and a high feed-back error. For the feed-forward method the spring constant, moving mass and damping of the optical guide and its geometry may need to be determined first. These parameters can determine in a unique way the position and speed depending on the applied force. This force is a function of the applied current. The feed-forward term may e.g. be implemented as a look up table containing known relationships between mechanical or electrical parameters and the movement of the optical probe. Such relationships may be known from idealized tests.

Figure 6:
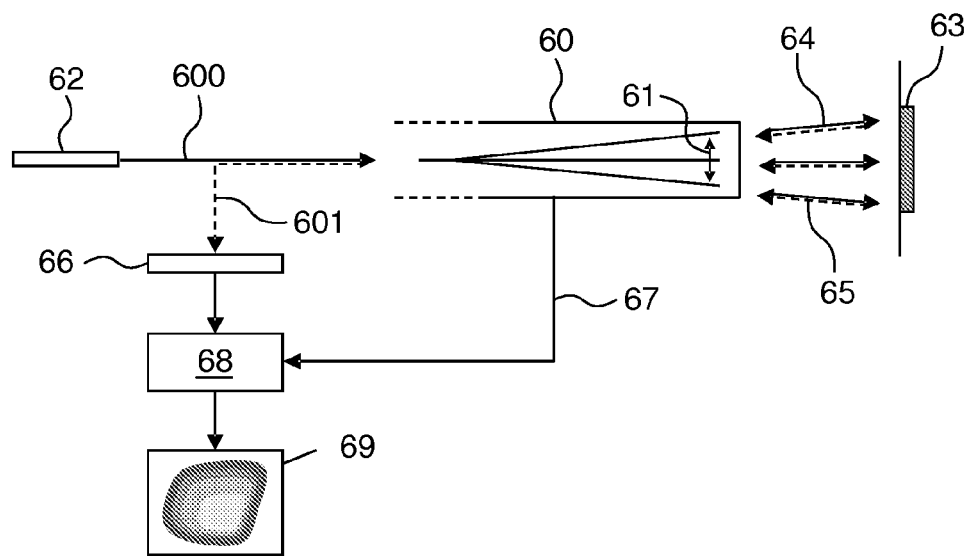
FIG. 6 schematically illustrates the operation of an embodiment of the optical probe in connection with an optical imaging system.

FIG. 6 schematically illustrates the operation of an embodiment of the optical probe in connection with an optical imaging system.

FIG. 6 schematically illustrates an optical probe 60, e.g. as illustrated in connection with FIGS. 1 and 2. The displacement of the probe is schematically indicated 61. The optical probe is optically coupled to a radiation source 62 so that the probe guides radiation 600, 64 from the radiation source to a region of interest 63. The radiation source may be any suitable source, such as but not limited to any type of laser, LEDs, gas-discharge lamps or luminescence sources.

The radiation emitted 64 from the probe interacts with the object under investigation in the region of interest 63. After interaction, part of the radiation 65 may be received by the probe, e.g. the reflected radiation, back-scattered radiation, re-emitted radiation, or any other type of radiation. The detected radiation 65, 601 may via coupling from the probe be directed to a detector 66.

The detected radiation 65 may together with positional data 67 as is known from the position generator 34 (FIG. 3) be inputted into an image construction unit 68 for generating an image 69 of the region of interest.

Due to the feedback and optionally feed-forward correction of the drive current, the generated image is without, or at least minimized with respect to, positional distortion. The positional correction offered by embodiments of the present invention force the optical probe to follow the pre-set or desired path, and the actual position closely matches the pre-set position of the optical probe during the displacement or scanning of the probe.

The invention can be implemented by means of hardware, software, firmware or any combination of these. The invention or some of the features thereof can also be implemented as software running on one or more data processors and/or digital signal proces The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

Although the present invention has been described in connection with the specified embodiments, it should not be construed as being in any way limited to the presented examples. The scope of the present invention is to be interpreted in the light of the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. An optical probe (1, 20), the probe comprising
an optical guide (2, 25) having a distal end (3);
a housing (4, 22), the optical guide being mounted inside the housing so that the distal end is displaceable with respect to the housing; and
a coil-based actuation system (9, 10, 21, 23) comprising drive coils (9, 23) capable of displacing the distal end by a displacement force induced by driving a drive current through the drive coils; wherein the drive current comprises a set-point current related to a positional set-point and an adjustment term;
wherein the adjustment term is determined by a feedback loop comprising:
applying the drive current to the drive coils;
temporally switching off the drive current and while the drive current is switched off measure a speed of the distal end; and
comparing the positional set-point and the measured speed by either
deriving from the positional set-point a set-point speed and comparing the set-point speed and the measured speed to derive a difference; or
deriving from the measured speed a measured position, and comparing the positional set-point and the measured position to derive a difference,
and adjusting the drive current if the difference is above a preset level.

2. The probe according to claim 1, wherein the speed of the distal end is measured by measuring the voltage (26) across the drive coils (23) while the drive current is switched off.

3. The probe according to claim 1, wherein the speed of the distal end is measured by switching on a measurement circuit adapted to measure the speed of the distal end, while the drive current is temporally switched off.

4. The probe according to claim 1, wherein the drive current is adapted to displace the optical guide at a frequency substantially equal the resonance frequency of the probe.

5. The probe according to claim 1, wherein the loop gain of the feedback loop is larger than 1.

6. The probe according to claim 1, wherein the actuation system comprises a first part comprising an axially polarized magnet (10, 21) and a second part comprising electromagnetic coils (9, 23); wherein one of the first and second parts is mounted on the housing (4, 22) and the other of the first and second parts is mounted on the optical guide (2, 25).

7. The probe according to claim 1, wherein the adjustment term further comprises a feed-forward term, the feed-forward term being based on one or more mechanical and/or electrical parameters.

8. The probe according to claim 1, wherein the optical guide is an optical fibre with a free distal end.

9. The probe according to claim 1, wherein the probe is part of an endoscope, a catheter, a needle or biopsy sample system.

10. An optical imaging system comprising:
an optical probe (60) according to claim 1;
an radiation source (62) optically coupled to the optical probe, the probe being arranged for guiding radiation (64, 600) emitted from the radiation source to a region of interest (63); and
a radiation detector (66) optically coupled to the optical probe, the detector being arranged for detecting radiation (65, 601) received from the region of interest.

11. A method of operating a probe (1, 20);
the probe comprising:
an optical guide (2, 25) having a distal end (3);
a housing (4, 22), the optical guide being mounted inside the housing so that the distal end is displaceable with respect to the housing; and
a coil-based actuation system (9, 10, 21, 23) comprising drive coils (9, 23) capable of displacing the distal end by a displacement force induced by driving a drive current through the drive coils; wherein the drive current comprises a set-point current related to a positional set-point and an adjustment term;
wherein the method comprising:
applying the drive current to the drive coils;
temporally switching off the drive current and measuring the speed of the distal end; and
comparing the positional set-point and the measured speed by either
deriving from the positional set-point a set-point speed and comparing the set-point speed and the measured speed to derive a difference; or
deriving from the measured speed a measured position, and comparing the positional set-point and the measured position to derive a difference;
and adjusting the drive current if the difference is above a preset level.

* * * * *